United States Patent [19]

Kimble

[11] 4,322,550

[45] Mar. 30, 1982

[54] RECOVERY OF MERCAPTOALKANOIC ACIDS USING ALKYLENE GLYCOL ETHERS

[75] Inventor: James B. Kimble, Bartlesville, Okla.

[73] Assignee: Phillips Petroleum Company, Bartlesville, Okla.

[21] Appl. No.: 193,871

[22] Filed: Oct. 3, 1980

[51] Int. Cl.³ .................. C07C 148/04; C07C 149/20; C07C 149/22; C07C 149/26
[52] U.S. Cl. .................................. 562/512; 260/399; 562/504; 562/505; 562/506; 562/507
[58] Field of Search ................ 562/512, 507, 504–506; 260/399

[56] References Cited

U.S. PATENT DOCUMENTS

| | | | |
|---|---|---|---|
| 2,413,361 | 12/1946 | Martin | 562/512 |
| 2,594,030 | 4/1952 | Coons et al. | 562/512 |
| 3,029,279 | 4/1962 | Kondo | 562/512 |
| 3,927,085 | 12/1975 | Zengel et al. | 562/512 |

FOREIGN PATENT DOCUMENTS

| | | | |
|---|---|---|---|
| 695493 | 8/1953 | United Kingdom | 562/512 |
| 194812 | 6/1967 | U.S.S.R. | 562/512 |

*Primary Examiner*—Vivian Garner

[57] ABSTRACT

Various mercaptoalkanoic acids are recovered from an aqueous medium or water in which they are contained by a liquid-liquid solvent extraction operation employing at least one of an alkanoic acid ester and an alkylene glycol ether. In one embodiment, thioglycolic acid has been extracted with ethyl acetate. In another embodiment, it has been recovered with ethylene glycol monoethyl ether acetate. In a further embodiment, it has been recovered with diethylene glycol diethyl ether.

5 Claims, No Drawings

RECOVERY OF MERCAPTOALKANOIC ACIDS USING ALKYLENE GLYCOL ETHERS

BRIEF DESCRIPTION OF INVENTION

Mercaptoalkanoic acids are extracted from an aqueous medium by a liquid solvent extraction using at least one of an alkanoic acid ester and an alkylene glycol ether.

DETAILED DESCRIPTION

This invention relates to the recovery of a mercaptoalkanoic acid. In one of its aspects, it relates to extraction of such an acid from water. In a further aspect of the invention, it relates to the provision of solvents which act selectively as to remove a mercaptoalkanoic acid from an aqueous medium by solvent extraction.

In one of its concepts, the invention provides a process for the extraction of a mercaptoalkanoic acid from an aqueous medium which comprises subjecting the said medium to liquid-liquid solvent extraction and employing at least one of an alkanoic acid ester and an alkylene glycol ether.

Mercaptoalkanoic acids such as β-mercaptopropionic acid and mercaptoacetic acid (thioglycolic acid) are useful industrial chemicals serving as intermediates in such application areas as polymers for sealants, adhesives and coatings, hair-waving lotions, depilating agents, wool treating agents, etc. The most widely used in thioglycolic acid whose synthesis is well known. For example, U.S. Pat. No. 3,927,085, issued Dec. 16, 1975, describes the synthesis of thioglycolic acid by reacting $H_2S$, chloroacetic acid and aqueous ammonium hydroxide. The reaction is followed by acidification with sulfuric acid and extraction with an organic solvent such as diisopropyl ether and finally separation of the product by distillation. Likewise, U.S. Pat. Nos. 2,413,361 and 2,594,030, issued Dec. 31, 1946 and Apr. 22, 1952, respectively, describe a similar type of synthesis wherein each method involves the separation of thioglycolic acid from an aqueous medium using a solvent such as butyl or isopropyl ether. The instant invention provides solvents of improved selectivity to extract thioglycolic acid from water. Thus, solvents such as alkanoic acid esters and alkylene glycol ethers significantly increase the rate of separation as well as the amount of thioglycolic acid separated from an aqueous medium compared to the solvents of the above-mentioned references, disclosures of which are incorporated herein. The solvents of the invention are less hazardous. They are less flammable and they do not form explosive peroxides as can the commonly used ethers.

It is the object of this invention to recover a mercaptoalkanoic acid from water or an aqueous medium. It is a further object of the invention to provide a liquid-liquid solvent extraction process having improved rates of extraction to extract a mercaptoalkanoic acid from water or an aqueous medium in which it is found. A still further object of the invention is to provide for improved recovery of the mercaptoalkanoic acid from an aqueous medium or from water in which it is found. It is still a further object of the invention to provide at least one solvent novel for the liquid-liquid solvent extraction of a mercaptoalkanoic acid from an aqueous medium or water.

Other aspects, concepts, objects and several advantages of the invention are apparent from a study of this disclosure and the appended claims.

According to the present invention, a mercaptoalkanoic acid is recovered by liquid-liquid solvent extraction from an aqueous medium or water in which it is found employing as solvent for the extraction at least one of an alkanoic acid ester and an alkylene glycol ether.

Mercaptoalkanoic acids useful in this invention are those materials represented by the formula $$HS-R-COOH \qquad (I)$$

wherein R can be any alkylene or cycloalkylene group having from one to twelve carbon atoms. Exemplary of these compounds are, for example, mercaptoacetic acid (thioglycolic acid)
2-mercaptopropionic acid (thiolactic acid)
3-mercaptopropionic acid (β-thiolactic acid)
4-mercaptobutyric acid
3-mercaptoisobutyric acid
2-mercaptoisobutyric acid
2-mercaptovaleric acid
3-mercaptoisovaleric acid
2-mercaptohexanoic acid
6-mercaptohexanoic acid
2-mercaptododecanoic acid
12-mercaptododecanoic acid
2-mercaptocyclohexanecarboxylic acid
4-mercaptocyclohexanecarboxylic acid The liquid extraction solvents useful in this invention are those materials represented by formulas II or III, $$R'CO_2R_1 \qquad (II)$$

$$R_3O(R_2O)_nR_4 \qquad (III)$$

wherein R' is an alkyl or cycloalkyl group having one to twelve carbon atoms; $R_1$ can be any alkyl group having from one to six carbon atoms; $R_2$ can be any alkyl group having one to four carbon atoms; $R_3$ can be any alkyl group having from two to six carbon atoms; $R_4$ can be any alkanoyl radical having from two to twelve carbon atoms or $R_4$ can be $R_3$ as herein defined, and n can be any integer from 1 to 6. Exemplary of compounds represented by formula II are, for example methyl acetate (methyl ethanoate)
ethyl acetate
propyl acetate
hexyl acetate
methyl propanoate
ethyl butanoate
propyl hexanoate
methyl dodecanoate
hexyl dodecanoate Exemplary of compounds represented by formula III are, for example, ethylene glycol diethyl ether
ethylene glycol dipropyl ether
ethylene glycol dihexyl ether
diethylene glycol diethyl ether (diethyl Carbitol)
diethylene glycol dihexyl ether
propylene glycol diethyl ether
dipropylene glycol diethyl ether
butylene glycol diethyl ether
dibutylene glycol diethyl ether
triethylene glycol diethyl ether tetraethylene glycol diethyl ether
hexaethylene glycol diethyl ether
ethylene glycol monoethyl ether acetate (Cellosolve acetate)
ethylene glycol monoethyl ether propanoate
ethylene glycol monoethyl ether hexanoate
ethylene glycol monoethyl ether dodecanoate
diethylene glycol monoethyl ether acetate
tripropylene glycol monopropyl ether propanoate The liquid extraction solvents disclosed herein can be prepared by well-known methods. For example, compounds corresponding to Formula II can be simply prepared by an esterification process wherein an alkanoic acid is reacted with an alcohol in the presence of a catalyst. Likewise dialkyl glycol ethers corresponding to formula III can also be prepared by first reacting an alcohol with an alkylene oxide and this monoether glycol product further reacted with an alkylene oxide to the desired value of n as shown in formula III. This new monoether glycol can then be converted to the alkali metal salt and reacted with an alkyl halide to give the desired diether product. Ether esters corresponding to formula III are similarly prepared as described for the diether glycols with the exception that the monoether glycol intermediate is reacted with a carboxylic acid in an esterification process.

The extraction process herein described can be conducted in any known type equipment suitable for liquid-liquid extractions. The extraction can be carried out generally at about ambient room temperature but can also be conducted above room temperature (e.g., 30° C. to 50° C.) if desired. Likewise pressure is not particularly critical in this invention. Pressure varying from atmospheric to about 200 psig are thought to be desirable.

The following examples serve to illustrate the operability of this invention.

EXAMPLE I

This example is a control illustrating the general procedure used to evaluate the extraction efficiency of chloroform in removing thioglycolic acid from an aqueous solution. A stock solution was prepared simulating a typical product effluent from the synthesis of thioglycolic acid from chloroacetic acid, ammonium bisulfide and water, namely 921 grams (10 moles) thioglycolic acid, 1322 grams (10 moles) ammonium sulfate, and 535 (10 moles) ammonium chloride diluted with water to 5 liters of solution. A 250 milliliter aliquot of this stock solution was extracted at ambient room temperature, once with 100 milliliters of chloroform and then three times with 50 milliliter portions of chloroform. Each extract was then analyzed by GLC to determine the amount of thioglycolic acid present. This analysis was conducted as follows: a one milliliter sample of extract was added to a vial which contained one milliliter of a solution prepared by dissolving one gram of diphenyl ether in 50 milliliters of pyridine. To this vial was then added 0.5 milliliters of N,O-Bis(trimethylsilyl)trifluoroacetamide, available from Aldrich Chemical Co., and the mixture warmed at 50° C. for 30 minutes. After cooling to room temperature, a few microliters were injected into a chromatograph machine equipped with a 121.9 cm (4 ft)×0.635 cm (0.25 in.) column packed with 10 weight percent Carbowax 200 on Chromosorb P and heated isothermally at 140° C. The amount of thioglycolic acid was then determined by computer using diphenyl ether as an internal standard. In this manner, it was estimated that the following amounts of the original thioglycolic acid were now present in each fraction; fraction 1, 15.2 weight percent; fraction 2, 7.3 weight percent; fraction 3, 7.0 weight percent; fraction 4, 6.3 weight percent for a total of 35.8 weight percent thioglycolic acid recovered (extracted) from the original aqueous solution.

EXAMPLE II

Using the general procedure described in Example I, several other extraction liquids were evaluated. These results along with the chloroform results in Example I are listed in Table I wherein it is shown that certain type liquids such as chloroform and ethers (Runs 1 through 4) are not as efficient as other type liquids such as alkanoic acid esters or alkylene glycol ethers (Run 5 through 7) in removing thioglycolic acid from an aqueous medium. In addition, the data shows the inventive liquids (Runs 5 through 7) remove thioglycolic acid from water at a faster rate than with the control liquids (Runs 1 through 4).

TABLE I

EFFECT OF LIQUID (SOLVENT) EXTRACTION OF THIOGLYCOLIC ACID FROM WATER[a]

| Run No. | Liquid (Solvent)[e] | Recovered Thioglycolic Acid[b] Extractions | | | | | |
|---|---|---|---|---|---|---|---|
| | | 1 | 2 | 3 | 4 | 5 | Total |
| Control Runs: | | | | | | | |
| 1. | Chloroform | 15.2 | 7.3 | 7.0 | 6.3 | — | 35.8 |
| 2. | n-Butyl Ether | 6.8 | 6.0 | 6.0 | 5.7 | 5.5 | 29.5 |
| 3. | n-Butyl Phthalate | 12.1 | 10.1 | 9.2 | 7.4 | 6.9 | 45.7 |
| 4. | Diethyl Ether | 42.5 | 21.4 | 13.4 | 8.0 | 5.2 | 90.5 |
| Inventive Runs: | | | | | | | |
| 5. | Ethyl Acetate | 49.2 | 25.4 | 14.7 | 7.0 | 3.7 | 100.0 |
| 6. | Cellosolve Acetate[c] | 55.8 | 27.8 | 10.9 | 3.7 | 1.9 | 100.1 |
| 7. | Diethyl Carbitol[d] | 65.0 | 26.0 | 6.7 | 1.9 | 0.4 | 100.0 |

[a]A 250 milliliter solution comprised of 46.05 grams thioglycolic acid, 66.1 grams $(NH_4)_2SO_4$ and 26.7 grams $NH_4Cl$ diluted to 250 milliliters with water.
[b]Determined by GLC.
[c]Ethylene glycol monoethyl ether acetate.
[d]Diethylene glycol diethyl ether.
[e]With the exception of Run No. 3, each extraction was with 50 mL of the indicated solvent.

It is evident that from the foregoing that having discovered, generally, the selected solvency of the specifically employed solvents as herein disclosed, it is apparent that a class of acids can be effectively recovered employing the classes of solvents as herein disclosed and claimed. Thus, the runs made are considered a basis for the invention as disclosed, as evidenced by the data given. Thus, viewing the data, it is evident that there is a real, significant improvement not only in rate of thioglycolic acid removal but also in the recovery thereof over such solvents as n-butyl phthalate, chloroform and n-butyl ether. Indeed, even such a good solvent as diethyl ether is considerably and significantly exceeded by the three solvents of the invention draft namely, ethyl acetate, Cellosolve acetate and diethyl Carbitol.

It is evident that the term alkylene glycol ether includes such an ether having at least one ester group, e.g., ethylene glycol monoethyl ether acetate.

Reasonable variation and modification are possible with the scope of the foregoing disclosure and the appended claims to the invention, the essence of which is that a mercaptoalkanoic acid is selectively removed or extracted in a liquid-liquid solvent extraction process employing at least one of an alkanoic acid ester and an alkylene glycol ether as selective solvents, as herein described.

I claim:

1. A process for the liquid-liquid solvent extraction of a mercaptoalkanoic acid represented by the formula: HS-R-COOH wherein R is an alkylene or cycloalkylene group having from one to twelve carbon atoms, from an aqueous medium or water in which it is found which comprises subjecting the medium containing said acid to liquid-liquid solvent extraction conditions employing an alkylene glycol ether represented by the formula: $R_3O(R_2O)_nR_4$ wherein $R_3$ is an alkyl group having from 2 to 6 carbon atoms, $R_2$ is an alkyl group having from 1-4 carbon atoms, $R_4$ is an alkanoyl radical having 2 to 12 carbon atoms or can be $R_3$ as herein defined and wherein n is an integer in the range of 1-6.

2. A process according to claim 1 wherein the mercaptoalkanoic acid is at least one of the following: mercaptoacetic acid, 2-mercaptopropionic acid, 3-mercaptopropionic acid, 4-mercaptobutyric acid, 3-mercaptoisobutyric acid, 2-mercaptoisobutyric acid, 2-mercaptovaleric acid, 3-mercaptoisovaleric acid, 2-mercaptohexanoic acid, 6-mercaptohexanoic acid, 2-mercaptododecanoic acid, 12-mercaptododecanoic acid, 2-mercaptocyclohexanecarboxylic acid, and 4-mercaptocyclohexanecarboxylic acid.

3. A process according to claim 1 wherein the alkylene glycol ether is at least one of the following: ethylene glycol diethyl ether, ethylene glycol dipropyl ether, ethylene glycol dihexyl ether, diethylene glycol diethyl ether, diethylene glycol dihexyl ether, propylene glycol diethyl ether, dipropylene glycol diethyl ether, butylene glycol diethyl ether, dibutylene glycol diethyl ether, triethylene glycol diethyl ether, tetraethylene glycol diethyl ether, hexaethylene glycol diethyl ether, ethylene glycol monoethyl ether acetate, ethylene glycol monoethyl ether propanoate, ethylene glycol monoethyl ether hexanoate, ethylene glycol monoethyl ether dodecanoate, diethylene glycol monoethyl ether acetate, and tripropylene glycol monopropyl ether propanoate.

4. A process according to claim 1 wherein the mercaptoalkanoic acid recovered is at least one of the following: 2-mercaptopropionic acid, 3-mercaptopropionic acid, 4-mercaptobutyric acid, and 3-mercaptoisobutyric acid.

5. A process according to claim 4 wherein the solvent employed is ethylene glycol monoethyl ether acetate or diethylene glycol diethyl ether.